United States Patent
Ding et al.

(10) Patent No.: US 6,768,923 B2
(45) Date of Patent: Jul. 27, 2004

(54) APPARATUS AND METHOD FOR VENTRICULAR PACING TRIGGERED BY DETECTION OF EARLY VENTRICULAR EXCITATION

(75) Inventors: Jiang Ding, Maplewood, MN (US); Andrew P. Kramer, Stillwater, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 320 days.

(21) Appl. No.: 10/004,695

(22) Filed: Dec. 5, 2001

(65) Prior Publication Data

US 2003/0105492 A1 Jun. 5, 2003

(51) Int. Cl.[7] ............................................... A61N 1/368
(52) U.S. Cl. ........................................................ 607/9
(58) Field of Search ............................. 607/9; 600/509, 600/521

(56) References Cited

U.S. PATENT DOCUMENTS

| 4,589,420 A | * | 5/1986 | Adams et al. ............... 600/515 |
| 4,630,204 A | * | 12/1986 | Mortara ....................... 600/516 |
| 4,751,931 A | * | 6/1988 | Briller et al. ................ 600/513 |
| 5,313,953 A | * | 5/1994 | Yomtov et al. .............. 600/508 |
| 5,609,158 A | * | 3/1997 | Chan ........................... 600/518 |
| 6,267,778 B1 | * | 7/2001 | Cohen ............................. 607/9 |
| 6,609,027 B2 | * | 8/2003 | Kroll et al. ..................... 607/9 |

\* cited by examiner

Primary Examiner—Kennedy Schaetzle
(74) Attorney, Agent, or Firm—Thomas J. Nikolai; Nikolai & Mersereau, P.A.

(57) ABSTRACT

A pacing apparatus and method for providing optimum timing for ventricular pacing without referencing atrial activities. The pacing apparatus includes a processor, at least one sensor and a pulse generator. The pacing method includes the sensing of ventricular depolarization and the identification of an early electrical event, such as a depolarization of the HIS bundle or an onset of a ventricular depolarization (Q*). The system derives the proper timing using this early electrical event which provides a predictable relationship with an optimal ventricular pacing signal.

13 Claims, 3 Drawing Sheets

APPARATUS AND METHOD FOR VENTRICULAR PACING TRIGGERED BY DETECTION OF EARLY VENTRICULAR EXCITATION

BACKGROUND OF THE INVENTION

1. Field of the Invention

The present invention relates generally to a method and apparatus for coordinating the pacing of a heart and more particularly, to a method and apparatus for ventricular pacing that is triggered upon sensing an early ventricular event.

2. Description of the Related Art

Cardiac muscle needs to be electrically excited to depolarize causing a contraction. To depolarize, the muscle must reach a threshold voltage. Intrinsically, the threshold voltage is initiated by a nerve impulse. Once initiated, the depolarization wave propagates through the muscle causing the contraction. The depolarization can be recorded intracardially and/or extracardially. The recorded depolarization events are typically referred to as an electrocardiogram or ECG. An ECG recorded intracardially is more appropriately referred to as an electrogram. Typically, electrograms are recorded by electrodes placed endocardially in or epicardially on an atrium or ventricle. An ECG recorded extracardially is more appropriately referred to as a surface ECG. Surface ECGs are typically recorded from two or more electrodes placed at predetermined locations on a patient's skin. A complete surface ECG recording typically utilizes a conventional twelve lead configuration.

The features in a surface ECG are typically labeled according to the electrical activity's origin. The signal corresponding to the depolarization of the atria is called the P-wave. The signal corresponding to the depolarization of the ventricles is the QRS complex. The QRS complex can be described using three waves: the Q-wave; the R-wave; and the S-wave. The time interval from the P-wave to the R-wave is the PR interval. Thus, the PR interval is a measure of the delay between the electrical excitation in the atria and the ventricles.

Unlike surface ECG, electrograms mainly reflect local electrical depolarization. For example, an atrial electrogram mainly reflects the atrial depolarization. Therefore, an atrial electrogram corresponds to the P-wave in the surface ECG. Similarly, a ventricular electrogram mainly reflects ventricular depolarization, and thus, corresponds to a QRS complex of the surface ECG. However, it is quite often that the morphology of an electrogram may differ from its counterpart in a surface ECG, depending on the configuration of the recording electrode(s).

Currently, no consensus terminology describes the features of a ventricular electrogram. Borrowing terminology from surface ECGs, the largest peak in a ventricular electrogram is referred to as the R-wave, and the onset of the ventricular electrogram is referred to as the Q* point in the present disclosure. Physiologically, the Q* is considered the time of first or earliest detectable ventricular depolarization. Defined as the time of first detectable ventricular depolarization, the Q* concept can be applied to surface ECGs. Thus, the onset of the Q-wave in a surface ECG may be the first detectable ventricular depolarization coinciding with the Q* point of a ventricular electrogram. Thus, Q* may be measured from an electrogram or from a surface ECG.

Cardiac pacing has been used primarily to treat patients with bradycardia. A variety of pacing modes are used for the different syndromes of bradycardia. For example, for patients with normal atrial rhythm but slow ventricular rhythm due to $3^{rd}$ degree AV node block, VDD mode is often the choice of therapy. In the VDD pacing mode, ventricular pacing is triggered, after an AV delay, by a sensed electrical event in the atrium. Thus, the heart rate is increased and the ventricular rate is maintained at the atrial rate.

Recently, there has been increasing interest in using electrical stimulation as an alternative therapy to treat congestive heart failure (CHF) patients who are refractory to conventional drug therapy. For example, VDD pacing has been applied to CHF patients with normal heart rate, but with abnormal ventricular conduction system. In these patients, electrical stimulation has been used to correct the electric activation pattern of the ventricle(s) rather than to maintain the heart rate as it does for bradycardia patients. In theory, stimulating at an otherwise delayed portion of the ventricle restores synchronous ventricular contraction and thus, improves hemodynamic performance. Therefore, VDD stimulation for CHF is frequently referred to as cardiac resynchronization therapy (CRT). Currently, CRT is mainly applied to the left ventricle (LV) or both ventricles (biventricular or BV) for CHF patients with bundle branch block (BBB).

However, a large number of CHF patients also have chronic atrial fibrillation (AF). For those patients, VDD mode cannot be applied because of unavailable and/or unreliable atrial sensing to trigger ventricular stimulation. Biventricular triggering (BVT) has been developed to allow treatment of patients suffering from AF. In BVT, bi-ventricular stimulation is triggered upon sensing a ventricular event in either ventricle. In theory, BVT may still provide some degree of coordinated ventricular contraction. However, BVT mode is less likely than other methods to provide highly synchronous ventricular contraction because of a time delay between ventricular depolarization and triggering. That is, by the time current methods sense a ventricular event, usually from a R-wave as seen in a ventricular electrogram, a large portion of the ventricle may have already been intrinsically excited through asynchronous slow muscle propagation due to the block of the fast conduction system. Thus, a need exists for an alternative triggering event that is early enough to trigger ventricular stimulation and allows for more reliable sensing in the AF patients.

SUMMARY OF THE INVENTION

The method and apparatus of present invention meet the above described needs and provide additional advantages and improvements that will be recognized by those skilled in the art upon review of this disclosure. The present invention provides an apparatus and method for ventricular pacing triggered by an early ventricular sensed event. This early event occurs earlier than the R-wave and exists whenever there is intrinsic ventricular depolarization regardless of atrial conduction. The pacing pulse is delivered immediately or following a short delay to either or both ventricles upon detection of such an early event.

In its broadest aspects, the present invention comprises an apparatus including a sensor that is configured to sense the depolarizations of the heart, the sensor feeding data to a processor that is programmed to identify an early ventricular electrical event and a pulse generator controlled by the processor and configured to provide a pacing stimulus to at least one ventricle of the heart based upon the occurrence of the event. Possible early ventricular electrical events include the onset (Q*) of ventricular depolarizations which can be detected from QRS complex, and the onset of HIS bundle depolarization, which can be detected from a HIS bundle electrogram.

DETAILED DESCRIPTION OF THE INVENTION

The present invention provides an apparatus and method for ventricular pacing triggered by an early ventricular sensed event, such as the onset (Q*) of ventricular depolarization or the onset of HIS bundle depolarization. The apparatus and method provide a pacing pulse or series of pulses to one or both ventricles upon sensing this early event. For the purpose of the present invention, the Q* is defined as the first detectable onset of the QRS complex. The Q* point is typically obtained from an electrogram or a surface ECG. The onset of HIS bundle depolarization can be obtained from a HIS bundle electrogram.

Figure 1:
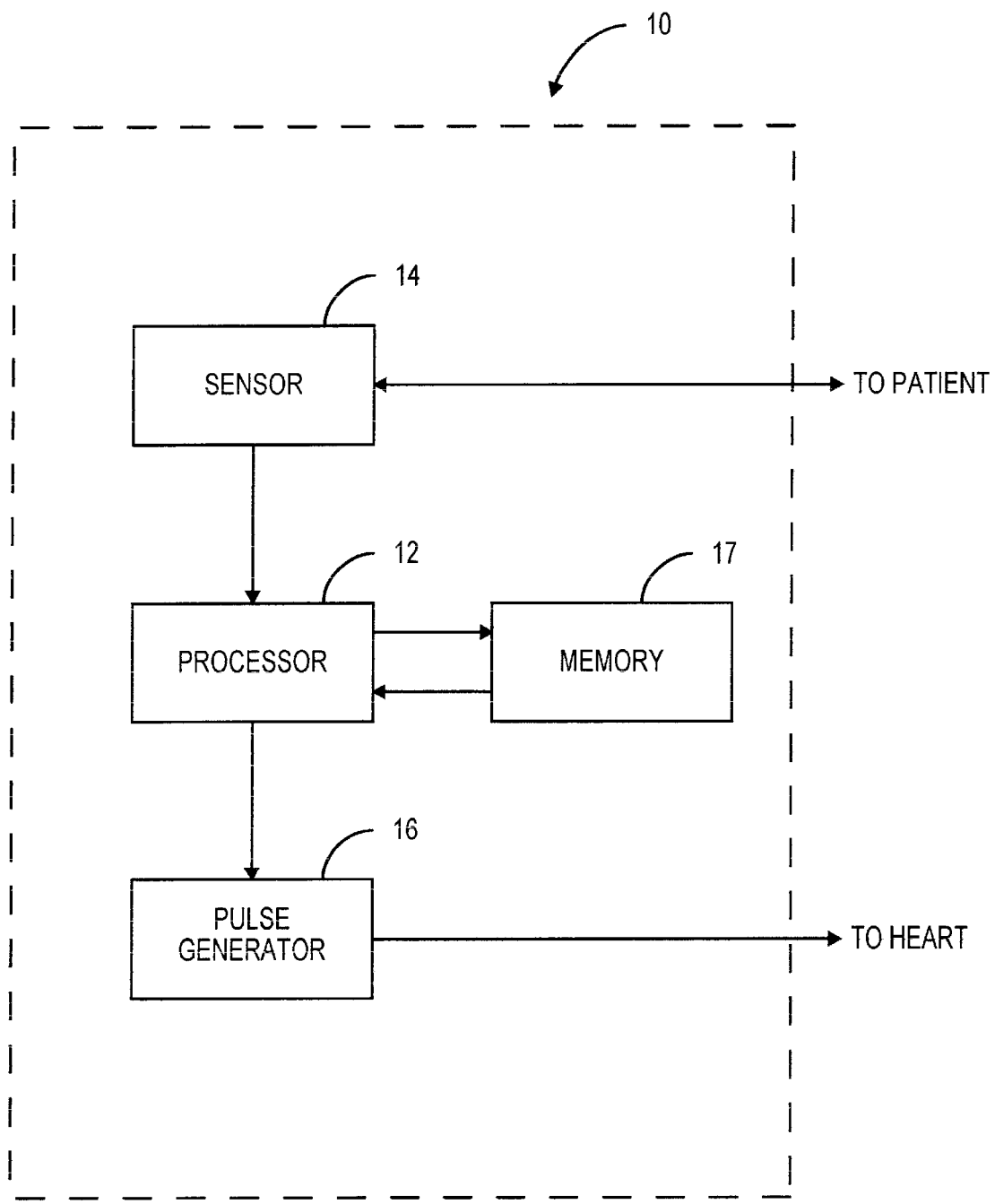
FIG. 1 is a block diagram of a pacing apparatus in accordance with the present invention.

The pacing method of the present invention may be carried out by any of a variety of pacing/defibrillation devices that can be either internal or external to the patient. A typical apparatus 10 in accordance with the present invention is shown in FIG. 1. Apparatus 10 includes a processor 12, at least one sensor 14, and a pulse generator 16. Processor 12 may be a microprocessor or a circuit configured to detect the Q* point of a QRS complex. Processor 12 may also include a memory 17 for storing data. Sensor 14 is configured to sense an electrogram or a surface ECG and condition the signal by amplification and filtering the record of Q* component of a QRS complex. Processor 12 receives data from sensor 14 and determines the time of occurrence of the Q* event. The processor then immediately or after a short period of time responds by sending a controlling signal to pulse generator 16 which directs at least one pacing stimulus pulse to one or both ventricles.

Figure 2:
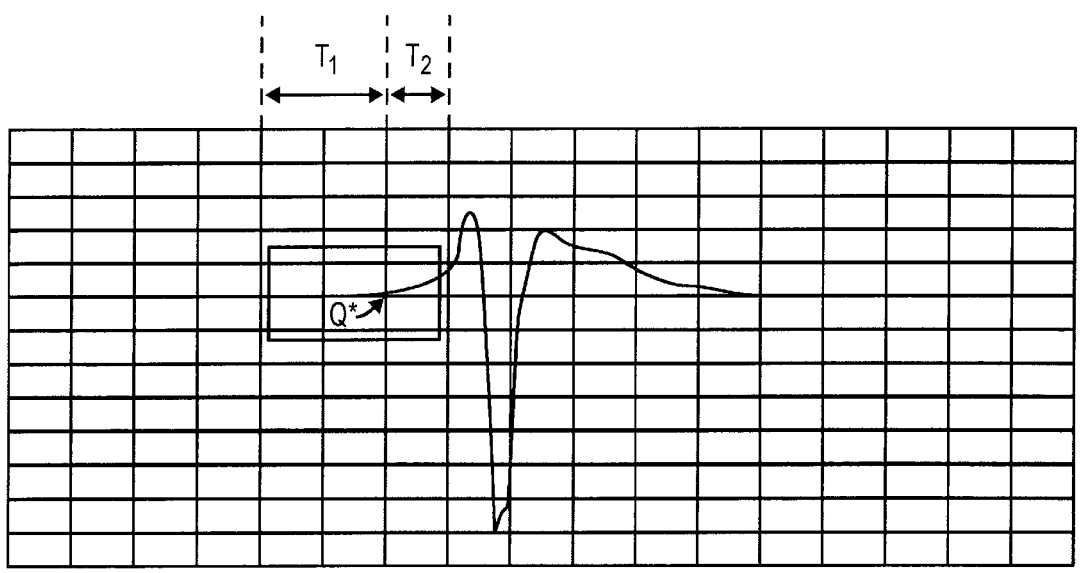
FIG. 2 is an electrogram illustrating one embodiment for detecting a Q* event.

When an electrogram is utilized, the electrogram is typically sensed using a unipolar sensing lead. The lead may be placed endocardially or epicardially. The use of a unipolar lead may provide a waveform more representative of a global depolarization event as shown in FIG. 2. A waveform representative of the global depolarization event simplifies the detection of the Q* event. However, a multipolar sensing lead may also be used with minor modifications to the below described detection methods, as will be recognized by those skilled in the art.

The processor may carry out any number of methods capable of establishing the Q* point in the cardiac cycle. For example, the Q* may be detected in real time based on a pre-established template. In one method, to detect the Q* based on a template, an ensemble-average is first calculated from digitized electrogram waveforms. The Q* is then established from the ensemble average. A template is established from the original ensemble-averaged waveform and a real time Q* is identified. Finally, ventricular pacing is triggered based on the identified real time Q* point.

The ensemble average may be performed by aligning a number (K) of normal QRS complexes having similar morphology at the peak of the R-wave. Typically, K is an integer between 20 and 50. The selection of normal QRS complexes can be done automatically by a device or manually by visual inspection. Typically, all the normal QRS complexes have regular R-to-R intervals, with differences among the intervals less than 10%. Therefore, the time relationship between the intervals of the R-waves may be used for automatic selection.

The Q* is then established from the ensemble-averaged waveform in accordance with several algorithms.

One such suitable algorithm may first calculate the absolute derivative of the ensemble-averaged waveform, and the results normalized by the maximum derivative. The algorithm would then mark the location of the R-wave of the ensemble-averaged waveform by searching for a largest peak.

Second, the algorithm may search for a flattest segment of the normalized derivative prior to the R-wave. This is typically done by calculating the mean and standard deviation (STD) of data points within a fixed-length window that moves away from the location of R-wave to the left (i.e. earlier than R-wave). The data related to the flattest segment of the normalized derivative has the minimum standard deviation over all the data within the window. The window length can be programmed to values between 20 to 100 ms. In one embodiment, the window length is set to 50 ms with satisfactory results. The algorithm may then set a threshold as the mean+STD of the flattest segment. The algorithm would then start from the flattest segment, examine each data point in the normalized derivative and compare it with the threshold. The Q* point is established as the first point after which there are no more than M consecutive data points whose values fall below the threshold. Typically, M is set to be a number that spans 2 to 5 ms in time. In one embodiment, the M value has been set to be equivalent to 4 ms. The location of Q* is then marked in the original ensemble-averaged waveform.

Third, the algorithm determines the template, the template being a segment of data from the original ensemble-averaged waveform. The template extends for a time, T1, leftwards and for a time, T2, rightwards from the Q* point (see FIG. 2). T1 and T2 can be programmed to fall in a range from 10 to 100 ms. In a typical embodiment, T1 may be 30 ms and T2 may be 20 ms. The corresponding number of data points in the template is N.

Fourth, the algorithm identifies the Q* in real time. Typically, a search for a Q* point begins about 200 ms after the R-wave of the previous beat (intrinsic) or 300 ms after the pacing pulse of the previous (stimulated) beat. Each incoming data point in the electrogram and all the past data points within a window (length=T1+T2) are cross-correlated with the template using the following equation:

$$corr(t) = \frac{\sum_{k=1}^{n}[Tmp(k) \times Egm(t-n+k)]}{\sqrt{\sum_{k=1}^{n}(Tmp(k))^2} \times \sqrt{\sum_{k=1}^{n}(Egm(t-n+k))^2}}$$

Where t is the current time, which is referenced to the R-wave (if intrinsic) or the pacing spike (if stimulated) of the previous beat; Egm(t) is the incoming electrogram data for the current beat; and Tmp(k) is the k-th point in the template, k=1, 2, ... n. The triggering point is found at time $t_Q$, when the following criteria are met:

i). corr($t_Q$)>$C_T$; and
   ii). Corr($t_Q$)≦Corr(t), where t is any data point within a small period of time, $T_3$, prior to $t_Q$ (i.e. $t_Q-T_3<t<t_Q$). $T_3$ is set to be between 5–10 ms, $C_T$ is a programmable threshold.

$C_T$ can typically be set between 0.75 and 0.9, depending on the noise level of the data. The $t_Q$ point may be later than the Q* point by an amount of about the value of $T_2$.

Fifth, the identification of the Q* triggers ventricular stimulation: One or more stimulation pulses are delivered to one or both ventricles at the time of $t_Q$. Typically, the delivery of the stimulation pulses is premised on the time difference between $t_Q$ and the reference point being between an upper rate pacing interval and a lower rate pacing interval. The reference point being either the peak of the R-wave from a previous intrinsic beat or the pacing spike from a previous paced beat.

Figure 3:
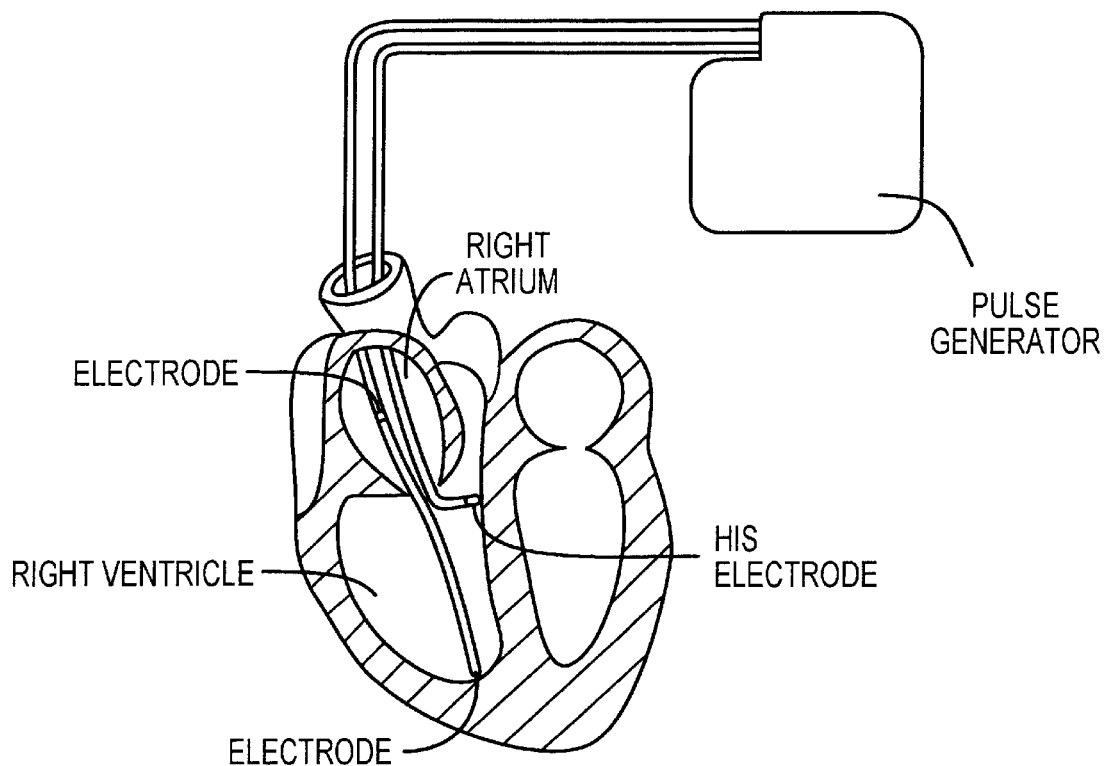
FIG. 3 is an embodiment apparatus in accordance with the present invention for detecting the onset of depolarization from the HIS bundle.
Figure 4:
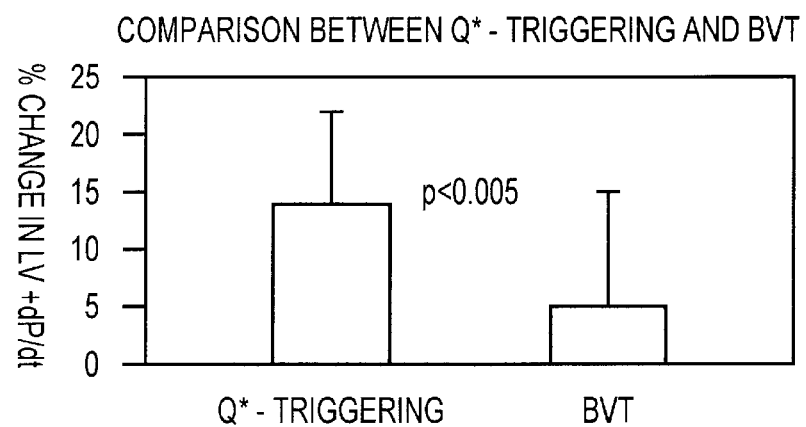
FIG. 4 is a graph showing a comparison of Q* triggered and BVT pacing.

Alternatively, the triggering point may be identified by an apparatus that includes an electrode which is placed in proximity to the HIS bundle to enable sensing of the HIS bundle electrical activity, as exemplified in FIG. 3. The sensor detects and records the signals being propagated by the HIS bundle. Typically, the output is called a HIS electrogram. Physiologically, the HIS bundle is depolarized prior to the major ventricular depolarization, thus, the HIS electrical event is earlier than the Q* as measured from a ventricular electrogram. However, triggering ventricular stimulation directly upon a HIS bundle event may produce even better ventricular coordination than triggering using Q*.

Due to different spectrums between HIS electrograms and ventricular electrograms, a special sensing amplifier may be used in the sensor 14 for detecting the HIS bundle activities. The characteristics of such amplifiers and the threshold crossing detection algorithms applicable to the present invention will be recognized by those skilled in the art upon review of this disclosure and literature. The following method relates only to the triggering of ventricular stimulation upon detection of a HIS bundle depolarization.

For each current beat, the detection for a HIS event starts about 200 ms after the R-wave of the previous beat (intrinsic) or 300 ms after the pacing spike of the previous beat (stimulated). In one embodiment, the HIS event is detected by the processor by electrogram signal threshold crossing. In another embodiment, the HIS event is detected by the processor using the template matching algorithm described for detecting Q*. Once a HIS event is detected, a triggering delay ($T_H$) is started. The value of $T_H$ can be programmed from 0 to 50 ms. The $T_H$ may typically be set to 0.0 ms. At the end of $T_H$, one or more stimulation pulses are delivered to one or both ventricles. Typically the delivery of stimulation pulses is premised on the time difference between the current delivery of stimulation and the reference point being between an upper rate pacing interval and a lower rate pacing interval. Again, the reference point is either the peak of the R-wave from a previous intrinsic beat or the pacing spike from a previous paced beat.

Some potential benefits of Q* triggered pacing over BVT have been retrospectively simulated through a study of 30 patients shown in FIG. 5. The data from the 30 patients under the PATH-CHF study were evaluated from the Q* triggered pacing's effectiveness relative to BVT pacing. In the study, all the patients were stimulated biventricularly with five AV delays during acute test.

Peak positive rate of change of left ventricular pressure during systole (abbreviated as LV+dp/dt) is a hemodynamic parameter that reflects left ventricular contractility (pumping power). Increases in LV contractility are observed in measurements as increases in LV+dp/dt. In this analysis, selected PATH-CHF patients responded to the biventricular stimulation therapy with an increase in LV+dP/dt of at least 5% over the sinus baseline. For each patient, a response curve was constructed which is the change in LV+dP/dt plotted against AV delays. To compensate for a discrete number (5) of paced AV delays in the actual trials, each response curve was interpolated by fitting through with a $4^{th}$ order polynomial. Then the timing for a Q* triggered stimulus or a BVT stimulus was converted into a corresponding AV delay, from which the outcome of the Q* triggered pacing or BVT pacing was obtained retrospectively from the response curve at the BV pacing mode. FIG. 5 illustrates the mean changes in LV+dP/dt that would be obtained from the Q* triggered pacing and the BVT pacing in the patients. These results demonstrate a greater increase in LV+dP/dt for the Q* triggered mode.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac rhythm management device, comprising:
   at least one sensor configured to sense an electrogram waveform representative of the depolarization of the heart;
   a processor receiving data from the sensor, wherein the processor is programmed to ensemble-average a digitized electrogram waveform over a predetermined number of QRS complexes and to derive therefrom the time of occurrence of an early electrical event (Q*) from the data by calculation of an absolute derivative of the ensemble-averaged electrogram waveform and normalizing the absolute derivative using a maximum absolute derivative of the ensemble-averaged electrogram waveform and locating a flattest segment of the normalized derivative of the absolute derivative of the ensemble-averaged electrogram within a window of a predetermined length to establish a threshold as a mean plus standard deviation of the flattest segment; and
   a pulse generator configured to provide a pacing stimulus to at least one ventricle in timed relation to the Q* event.

2. The device, as in claim 1, wherein the sensor is configured for placement in sensing proximity to a HIS bundle.

3. A device, as in claim 1, wherein the sensor is configured for placement in one or both ventricles.

4. A device, as in claim 1, wherein the sensor is configured to record an electrocardiogram.

5. A device, as in claim 4, wherein the sensor is configured to record a HIS bundle electrogram.

6. A device, as in claim 5, wherein the processor identifies the onset of HIS bundle depolarization.

7. A device, as in claim 6, wherein the processor identifies the onset of HIS bundle depolarization using template matching.

8. A device, as in claim 4, wherein the sensor is configured to record one of an epicardial electrogram and an endocardial electrogram.

9. A device, as in claim 8, wherein the sensor is configured to record the onset point (Q*) of an electrogram.

10. The device as in claim 1 wherein the Q* event is defined as the first data point in the normalized derivative of the ensemble-averaged electrogram waveform after which there are no more than a predetermined number of consecutive data points whose derivative values fall below said threshold.

11. A method for effecting CRT of AF patients, comprising:
   sensing the depolarization of one of the ventricles;
   identifying an early electrical event (Q*) in a sensed ventricular depolarization waveform by a template matching algorithm including the steps of:
   (i) calculating an ensemble-averaged waveform;
   (ii) establishing a Q* point on the ensemble averaged waveform;
   (iii) establishing a template; and
   (iv) matching a real time electrogram with the template to identify a real time Q* point; and
   triggering a pacing stimulus to one or both ventricles in timed relation to the identified event.

12. A method as in claim 11 wherein triggering occurs immediately upon the identification of a depolarization of the HIS bundle.

13. A method as in claim 11, wherein triggering occurs within between 1 and 50 ms of identifying a depolarization of the HIS bundle.

* * * * *